United States Patent [19]
Moller

[11] 4,182,871
[45] Jan. 8, 1980

[54] PROCESS FOR SPRAY DRYING SODIUM DICHLOROISOCYANURATE

[75] Inventor: Jens C. T. Moller, Bloustrød, Denmark

[73] Assignee: Niro Atomizer A/S, Denmark

[21] Appl. No.: 881,820

[22] Filed: Feb. 27, 1978

[51] Int. Cl.$^2$ .......... C07D 251/28
[52] U.S. Cl. .......... 544/190
[58] Field of Search .......... 544/190

[56] References Cited

U.S. PATENT DOCUMENTS

| | | | |
|---|---|---|---|
| 3,803,144 | 4/1974 | Berkowitz | 544/190 |
| 3,818,004 | 6/1974 | Berkowitz | 544/190 |
| 3,872,118 | 3/1975 | Berkowitz et al. | 544/190 |
| 3,888,855 | 6/1975 | Berkowitz | 544/190 |
| 3,951,972 | 4/1976 | Nelson et al. | 544/190 |
| 3,985,744 | 10/1976 | Manganaro | 544/190 |
| 3,988,336 | 10/1976 | Wojtowicz | 544/190 |

*Primary Examiner*—Dolph H. Torrence
*Attorney, Agent, or Firm*—Schuyler, Birch, McKie & Beckett

[57] ABSTRACT

A stable, free-flowing sodium dichloroisocyanurate dihydrate powder is prepared by spray drying an aqueous solution or slurry of sodium dichloroisocyanurate to form a particulate product having a moisture content from about 12.0 to about 20.0% by weight and subjecting this product to specific stabilizing and cooling after-treatment steps in a plurality of fluidized and/or vibrating beds. During the stabilizing step the product is dried to the final moisture level, if necessary, and the water of hydration is uniformly distributed and firmly bound to the particulate product.

19 Claims, 1 Drawing Figure

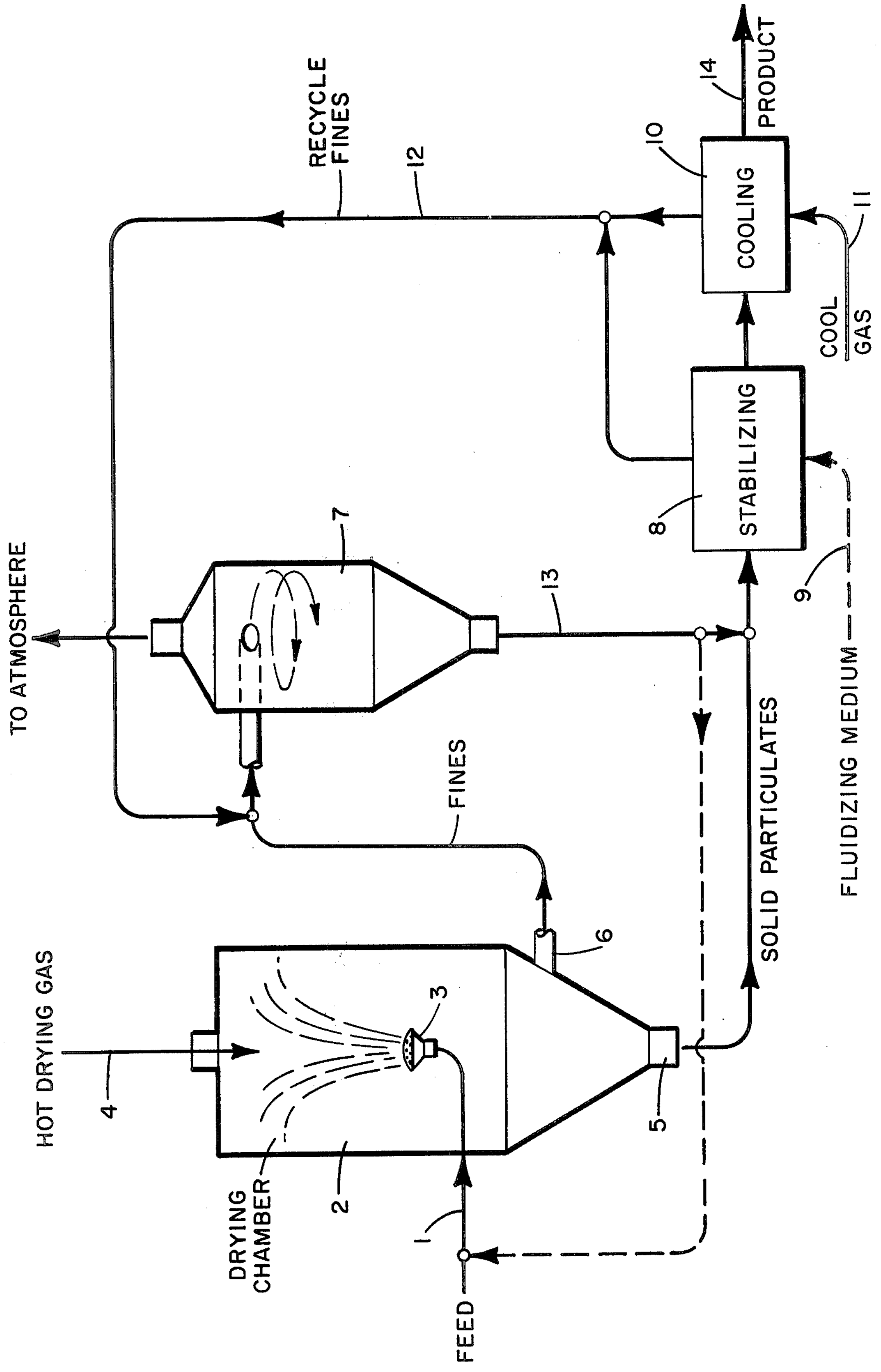
HOT DRYING GAS
4
DRYING CHAMBER
2
1
FEED
3
5
6
FINES
TO ATMOSPHERE
7
13
RECYCLE FINES
12
SOLID PARTICULATES
FLUIDIZING MEDIUM
9
8
STABILIZING
COOLING
10
11
COOL GAS
14
PRODUCT

PROCESS FOR SPRAY DRYING SODIUM DICHLOROISOCYANURATE

BACKGROUND OF THE INVENTION

1. Field of the Invention

The invention relates to a method of producing dry sodium dichloroisocyanurate dihydrate.

2. Description of the Prior Art

Alkali metal dichloroisocyanurates, especially the sodium salts, are widely known as a source of available chlorine in sanitizing and bleaching applications. These salts are known to exist in the anhydrous form and in the mono and dihydrate forms when associated with bound water. One of the major drawbacks of employing alkali metal dichloroisocyanurates is the property known as self propagating decomposition. It is known that when these compounds are exposed to high temperature source such as a spark or cigarette they can begin to burn and will continue until all of the material is consumed. It is known, however, that the presence of bound water of hydration lessens the tendency of alkali metal dichloroisocyanurates to decompose in this manner. The dihydrate form of these salts is the most desirable in this respect.

One reason why the dihydrate salt of sodium dichloroisocyanurate has not found wide commercial acceptance is the difficulty in manufacturing this product and more particularly problems associated with the drying step. The most common methods described for drying these salts are vacuum drying, drying in an air circulated oven, and spray drying. As noted in Wenzke, U.S. Pat. No. 3,289,312, none of these methods have provided any commercially acceptable product. Wenzke describes a process in which wet isocyanurate salt solids are fed to a pug mill to which dry anhydrous salt is added to reduce the free water content, followed by drying in a special chamber containing a cage-type mill through which a heated gas stream is flowing. This process is designed to produce an essentially anhydrous product.

Among other techniques proposed for drying this type of compound are the spray granulating process disclosed in Saeman, U.S. Pat. No. 4,005,087; the flash drying method described in Nelson, U.S. Pat. No. 3,951,972, the two-stage fluidized bed drying process described in Japanese Patent Publication No. 43-29,588, and the method of Goelz, U.S. Pat. No. 3,818,002, in which an aqueous solution or suspension of the salt is sprayed into a fluidized bed of dry salt particles and dried by the fluidizing gas. Goelz goes to great lengths to disparage both spray drying and fluidized bed drying of dichloroisocyanurate salts.

The alkali metal dichloroisocyanurate salts dried by the prior art methods have not proved commercially acceptable due to poor stability, and excessive caking and dusting.

Thus, it would be highly desirable to provide a method of drying sodium dichloroisocyanurate dihydrate and related salts which could produce a stable, free-flowing, non-dusting powder product.

BRIEF SUMMARY OF THE INVENTION

Therefore, it is an object of the present invention to provide a process for drying sodium dichloroisocyanurate dihydrate which does not suffer from the drawbacks of the prior art drying processes.

More specifically, it is an object of the present invention to produce a stable, free-flowing particulate product of sodium dichloroisocyanurate dihydrate which is substantially free of dust.

It is another object of the present invention to provide a process for drying sodium dichloroisocyanurate dihydrate which results in a product with little or no activity loss (i.e., available chlorine).

It is also an object of the present invention to produce a sodium dichloroisocyanurate dihydrate product with a uniformly bound water of hydration system.

These and other objects of the invention are achieved by a process for the production of a stable, free-flowing particulate sodium dichloroisocyanurate dihydrate product comprising the steps of (a) forming a particulate sodium dichloroisocyanurate product having a moisture content in the range of about 12.0 to about 13.5% by weight and a temperature of about 60° C. to about 80° C. by spraying an aqueous solution or slurry of sodium dichloroisocyanurate into a drying chamber and contacting the sodium dichloroisocyanurate spray with a heated drying gas flowing through said chamber;

(b) stabilizing said particulate product by agitating said product in a confined treating zone for a period of from about 1 to about 30 minutes, and at a temperature below which further reduction of the moisture content of said product will occur, whereby the water of hydration contained in said sodium dichloroisocyanurate product becomes uniformly distributed and firmly bound to said product;

(c) cooling the stabilized particulate product to a temperature below 40° C. in at least one fluidized and/or vibrating-fluidized bed; and (d) recovering a dry, stable, free-flowing particulate sodium dichloroisocyanurate dihydrate product from said cooling step.

The present invention further provides a process for the production of a stable, free-flowing particulate sodium dichloroisocyanurate dihydrate product comprising the steps of (a) forming a particulate sodium dichloroisocyanurate product having a moisture content in the range of about 13.5 to about 20.0% by weight and a temperature of about 60° C. to about 80° C. by spraying an aqueous solution or slurry of sodium dichloroisocyanurate into a drying chamber and contacting the sodium dichloroisocyanurate spray with a heated drying gas flowing through the chamber;

(b) stabilizing the particulate product by agitating the product in a confined treating zone for a period of from about 1 to 30 minutes, and at a temperature sufficient to reduce the moisture content of the product to a value in the range of about 12.0% to about 13.5% by weight whereby the water of hydration contained in the sodium dichloroisocyanurate product becomes uniformly distributed and firmly bound to the product;

(c) cooling the stabilized particulate product to a temperature below 40° C. in at least one fluidized or vibrating-fluidized bed; and (d) recovering a dry, stable, free-flowing particulate sodium dichloroisocyanurate dihydrate product from the cooling step.

BRIEF DESCRIPTION OF THE DRAWING

The FIGURE shows a schematic flow diagram of the process of the present invention.

DETAILED DESCRIPTION OF THE INVENTION

With reference to the FIGURE, in the first step of the process of the present invention a sodium dichloroisocyanurate-containing feed is supplied via line 1 to drying chamber 2. The feed material can be forwarded directly from a sodium dichloroisocyanurate reactor or it can be furnished from a tank (not shown) in which the solids content of the material can be adjusted to the proper level as described below. The feed material for the process of the present invention can comprise a solution or slurry of sodium dichloroisocyanurate. In the preferred embodiment the feed comprises an aqueous slurry also containing dissolved sodium dichloroisocyanurate solids. The feed material preferably contains from about 20 to about 65% by weight of total solids—i.e., both dissolved and undissolved. Most preferred is a total solids content in the range of from about 40% to about 58% by weight. In practice the solids employed can have a length of the needle crystal up to about 300 micron, with the majority below 50 micron. The slurry or solution of sodium dichloroisocyanurate is sprayed into drying chamber 2 by suitable means such as a spray nozzle 3 which is a standard nozzle giving a hollow cone spray pattern. Preferably, nozzle diameters are in the range of 0.7 to 3.0 mm. Such spray nozzles are commonly used in spray dryers for the drying of clay and ceramic materials.

A stream of heated drying gas 4 is provided to the drying chamber for contact with the spray of dichloroisocyanurate slurry or solution. Preferably, this drying gas comprises air at a temperature of about 200° C. to 250° C. Most preferred is a drying air inlet temperature of about 220° C. Other inert drying gases such as nitrogen, can of course be employed in the spray drying chamber. As a result of the contact between the spray of dichloroisocyanurate salt and the drying gas stream, a solid particulate product is produced. This particulate product is removed from the drying chamber via outlet 5. The product from the spray drying chamber should have a moisture content in the range of about 12.0% to about 20.0% by weight, and a temperature of about 60° C. to about 80° C. Drying air, which may contain some fine solid particles, is removed via outlet 6 and fed to cyclone separator 7, in which the fines are removed.

The solid particulate product from the drying chamber outlet is fed, preferably continuously, to confined treating zone 8 wherein the product is further dried, if necessary, and stabilized. In its broadest form the stabilization step comprises agitating the spray dried particles for a period of from about 1 to 30 minutes. Most preferred stabilization times are from about 3 to 10 minutes.

Where the residual moisture of the spray dried product is in the final target range of about 12.0 to about 13.5% by weight, the stabilization step should be performed at a temperature below which further moisture will be removed. In the preferred embodiment, this non-drying stabilization is effected in a confined treating zone which comprises a vibrating bed chamber in which externally applied vibration is employed to agitate the particles while moving them through the chamber. In another embodiment the confined treating zone for non-drying stabilization can comprise a fluidized or vibrating fluidized bed chamber. When employing this type of apparatus it is essential to keep the temperature of the fluidizing medium supplied to the chamber via inlet 9 (shown in phantom lines) below that which will effect further moisture removal. In most cases a fluidizing gas inlet temperature below about 20° C. will accomplish this result. The preferred fluidizing gas is air, although any inert gaseous medium can be employed.

Where the residual moisture of the spray dried product is in the range of about 13.5% to about 20.0% by weight, the stabilization step should be performed at a temperature sufficient to reduce the moisture level of the final product to a value in the range of about 12.0% to about 13.5% by weight. In the preferred embodiment the confined treating zone for effecting the drying/stabilizing is a fluidized or vibrating fluidized bed chamber. The gaseous fluidizing medium supplied to this chamber via line 9 should generally be at a temperature below 75° C. Preferred are fluidizing medium inlet temperatures of about 20° C. to 50° C. As discussed above, the preferred fluidizing medium is air although other inert gaseous materials may be employed. The confined treating zone for effecting the drying/stabilization can also comprise a two stage zone in which the particles are first further dried to the target range in a fluidized bed and then stabilized in a non-fluidized vibrating bed.

Whether or not additional excess moisture is removed, the stabilizing step serves to promote the uniform distribution of the water of hydration and further effects a binding or fixation of this water of hydration to the particulate product.

In the next step of the process of the present invention the stabilized particulate product is fed, preferably continuously, to cooling zone 10 where the temperature of the product is reduced to a value below about 40° C. Preferred are final product temperatures in the range of about 25° to about 40° C. In the preferred embodiment this cooling is accomplished in a fluidized or vibrating-fluidized bed chamber to which a cooled gaseous fluidizing medium is supplied via line 11. Fluidizing gas inlet temperatures of up to about 35° C. can be employed to accomplish the requisite product cooling. Most preferred are inlet temperatures of about 10° to about 30° C. The preferred fluidizing gas is air.

As shown in the FIGURE, any fines carried out of the stabilizing or cooling zones by the fluidizing gas streams can be returned via line 12 to the cyclone separator. The solids recovered from the cyclone can be supplied by line 13 to the stabilizer or to the feed system for reslurring in order to facilitate complete solids recovery.

In the final step of the process the stabilized and cooled product is recovered from outlet 14. This product retains high activity, i.e., available chlorine is above 54%. Moreover, the product produced by the present invention is highly stable under storage conditions and is more easily handled due to its free-flowing, non-dusting characteristics. The final product generally has a particle size in the range of from about 50 to 800 microns.

As indicated above, the stabilizing and cooling steps are preferably carried out in a fluidized, vibrating, or vibrating-fluidized bed chamber. While reference herein is made to single beds, it will be recognized by one skilled in the art that multi-stage beds or a plurality of beds may also be employed for the stabilizing and cooling steps. The most preferred type of bed is a vibrating-fluidized bed which can operate either with or without the fluidizing medium. This vibrating fluidized bed is standard commercial equipment of the type commonly used in processing spray dried milk powders and which has further applicability in the treating of paraformaldehyde powders, see U.S. Pat. No. 4,036,891. Typical of such equipment is the VIBRO-FLUIDIZER produced by Niro Atomizer, Inc. In this particular design of equipment fluidizing gas enters the bed at a velocity of 0.05 to 1.0 meters per second and preferably in the range of 0.2 to 0.5 meters per second.

The following specific example is intended to illustrate more fully the nature of the present invention without acting as a limitation on its scope.

EXAMPLE 1

A slurry with 55% solids by weight was introduced into a spray chamber and contacted with drying air at a temperature of 196° C. and dried to a powder which was removed from the bottom of the chamber at a temperature of 70° C. The powder had 17.2% residual moisture and was coarse (about 250 micron particle size) but was not free-flowing.

The dried powder was then further dried and stabilized in a vibrating fluidized bed with air at a temperature of 55° C. and a fluidization velocity of 0.33 m/s. The product was a non-dustry and free-flowing powder having 12.4% residual moisture and 55% available chlorine.

While certain specific embodiments of the invention have been described with particularity herein, it should be recognized that various modifications thereof will occur to those skilled in the art. Therefore, the scope of the invention is to be limited solely by the scope of the claims appended hereto.

I claim:

1. A process for the production of a stable, free-flowing particulate sodium dichloroisocyanurate dihydrate product comprising the steps of:

(a) forming a particulate sodium dichloroisocyanurate product having a moisture content in the range of about 12.0 to about 13.5% by weight and a temperature of about 60° C. to about 80° C. by spraying an aqueous solution or slurry of sodium dichloroisocyanurate spray with a heated drying gas flowing through said chamber;

(b) stabilizing said particulate product by agitating said product in a confined treating zone for a period of from about 1 to about 30 minutes, and at a temperature below which further reduction of the moisture content of said product will occur, whereby the water of hydration contained in said sodium dichloroisocyanurate product becomes uniformly distributed and firmly bound to said product;

(c) cooling the stabilized particulate product to a temperature below 40° C. in at least one fluidized or vibrating-fluidized bed; and (d) recovering a dry, stable, free-flowing particulate sodium dichloroisocyanurate dihydrate product from said cooling step.

2. The process of claim 1 wherein said sodium dichloroisocyanurate is sprayed into said drying chamber as a slurry also containing dissolved solids and having a total solids content of about 20% to about 65% by weight.

3. The process of claim 1 wherein said gas flowing through said drying chamber is air.

4. The process of claim 1 wherein said gas flowing through said drying chamber is introduced to said chamber at a temperature of from about 200° to about 250° C.

5. The process of claim 1 wherein said confined treating zone comprises at least one vibrating bed.

6. The process of claim 1 wherein said confined zone comprises at least one fluidized or vibrating fluidized bed and a gaseous fluidizing medium is supplied to said bed at a temperature of up to about 20° C.

7. The process of claim 6 wherein said gaseous fluidizing medium is air.

8. The process of claim 1 wherein the cooling of step (c) is effected by a gaseous fluidizing medium supplied to said fluidized or vibrating fluidized bed at a temperature of up to about 35° C.

9. The process of claim 8 wherein said gaseous fluidizing medium is air.

10. A process for the production of a stable, free-flowing particulate sodium dichloroisocyanurate dihydrate product comprising the steps of:

(a) forming a particulate sodium dichloroisocyanurate product having a moisture content in the range of about 13.5 to about 20.0% by weight and a temperature of about 60° C. to about 80° C. by spraying an aqueous solution or slurry of sodium dichloroisocyanurate into a drying chamber and contacting the sodium dichloroisocyanurate spray with a heated drying gas flowing through said chamber;

(b) stabilizing said particulate product by agitating said product in a confined treating zone for a period of from about 1 to 30 minutes, and at a temperature sufficient to reduce the moisture content of said product to a value in the range of about 12.0% to about 13.5% by weight whereby the water of hydration contained in said sodium dichloroisocyanurate product becomes uniformly distributed and firmly bound to said product;

(c) cooling the stabilized particulate product to a temperature below 40° C. in at least one fluidized or vibrating-fluidized bed; and (d) recovering a dry, stable, free-flowing particulate sodium dichloroisocyanurate dihydrate product from said cooling step.

11. The process of claim 10 wherein said sodium dichloroisocyanurate is sprayed into said drying chamber as a slurry also containing dissolved solids and having a total solids content of about 20% to about 65% by weight.

12. The process of claim 10 wherein said gas flowing through said drying chamber is air.

13. The process of claim 10 wherein said gas flowing through said drying chamber is introduced to said chamber at a temperature of from about 200° C. to about 250° C.

14. The process of claim 6 wherein said confined treating zone comprises at least one fluidized or vibrating-fluidized bed and a gaseous fluidizing medium is supplied to said bed at a temperature of up to about 75° C.

15. The process of claim 14 wherein said gaseous fluidizing medium is air.

16. The process of claim 14 wherein said gaseous fluidizing medium is supplied to said bed at a temperature of from about 20° C. to about 50° C.

17. The process of claim 10 wherein said confined zone comprises:

(i) at least one fluidized bed to which a gaseous fluidizing medium at a temperature of up to about 75° C. is supplied to effect reduction of the moisture content of said product, and (ii) at least one vibrating or vibrating fluidized bed in which the water of hydration is uniformly distributed and firmly bound to said product.

18. The process of claim 10 wherein the cooling of step (c) is effected by a gaseous fluidizing medium supplied to said fluidized or vibrating fluidized bed at a temperature of up to about 35° C.

19. The process of claim 18 wherein said gaseous fluidizing medium is air.

* * * * *